United States Patent [19]

Bhatt et al.

[11] Patent Number: 5,164,177
[45] Date of Patent: Nov. 17, 1992

[54] AQUEOUS HAIR STYLING AID

[75] Inventors: Darshna Bhatt, Schaumburg; Ramiro Galleguillos, Glendale Heights, both of Ill.

[73] Assignee: Helene Curtis, Inc., Chicago, Ill.

[21] Appl. No.: 716,709

[22] Filed: Jun. 18, 1991

[51] Int. Cl.⁵ .............................. A61K 7/11
[52] U.S. Cl. .......................... 424/47; 424/71; 424/DIG. 1; 424/DIG. 2
[58] Field of Search ............ 424/47, 71, DIG. 1, 424/DIG. 2, 78

[56] References Cited

U.S. PATENT DOCUMENTS

| | | | |
|---|---|---|---|
| 4,638,822 | 2/1987 | Grollier et al. | 424/71 |
| 4,673,569 | 6/1987 | Shernov et al. | 424/47 |
| 4,796,646 | 1/1989 | Grollier et al. | 424/47 |
| 4,839,167 | 6/1989 | Yamamoto et al. | 424/47 |

Primary Examiner—Thurman K. Page
Assistant Examiner—Amy Hulina
Attorney, Agent, or Firm—Marshall, O'Toole, Gerstein, Murray & Bicknell

[57] ABSTRACT

An aqueous aerosol or non-aerosol hair styling aid or mousse composition, and method, including a water-soluble or water-dispersable fixative resin in an amount of about 2% to about 40% by weight of the compositon, particularly about 2% to about 15% by weight of the composition; an electrolyte; water in an amount of about 30% to about 90% by weight of the composition; alcohol in an amount of 0% to about 30% by weight; and, with the aerosol compositions, a liquefied propellant gas, such as dimethyl ether, in an amount of about 5% to about 50% based on the total weight of the aerosol composition.

13 Claims, 1 Drawing Sheet

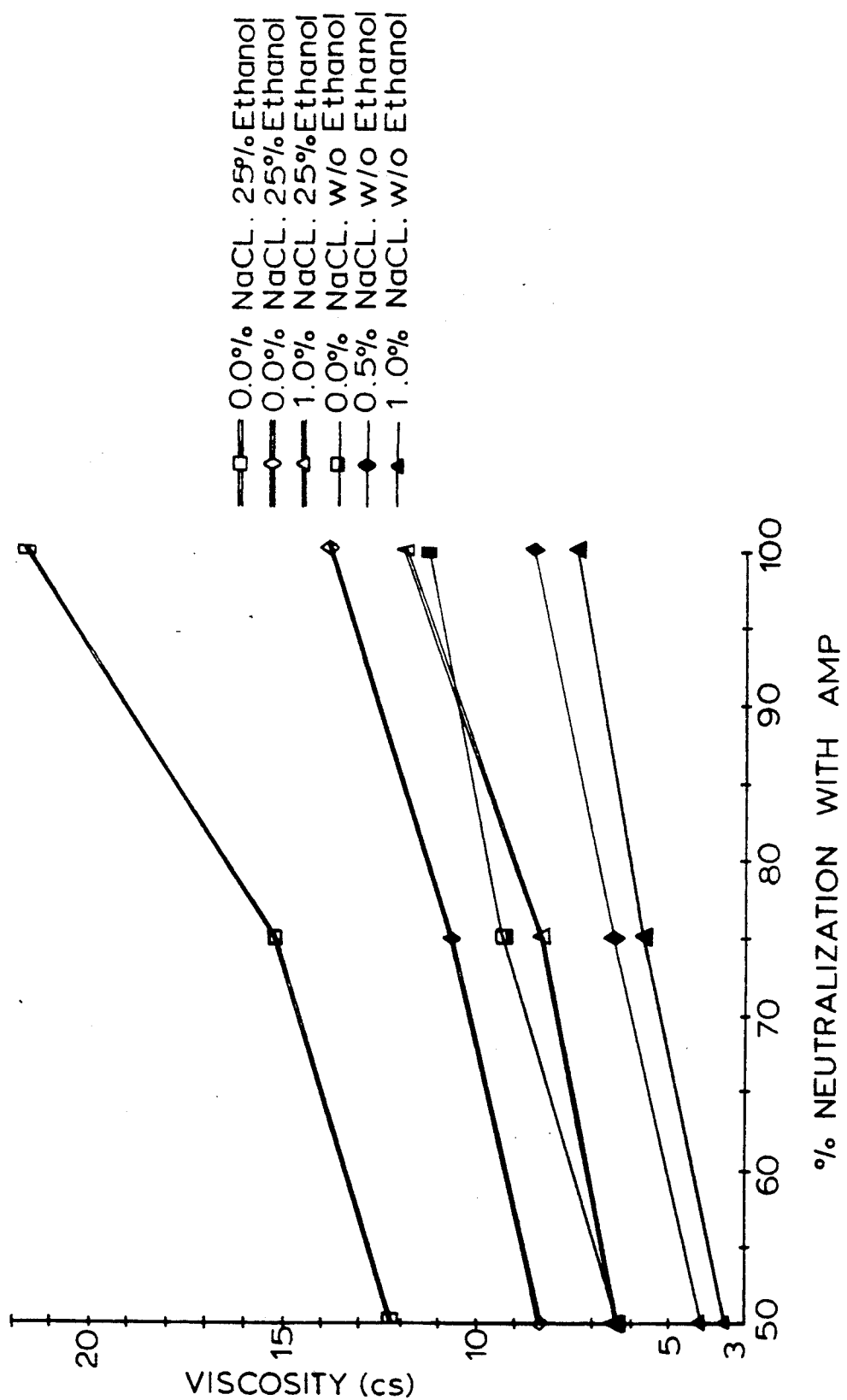

AQUEOUS HAIR STYLING AID

FIELD OF THE INVENTION

The present invention is directed to an aerosol or non-aerosol aqueous hair styling aid that is sprayed onto the hair from an aqueous composition, preferably an aerosol aqueous composition containing a propellant, to provide the hair with a particular shape or configuration. More particularly, the present invention is directed to an aqueous aerosol hair styling aid that has a very low percentage of volatile organic compounds and a high percentage of water, and is capable of homogeneously dispersing a relatively high percentage of a polymer, such as a fixative resin or gum, with or without a water evaporation agent, such as an alcohol, for example, ethanol.

BACKGROUND OF THE INVENTION AND PRIOR ART

Hair sprays provide human hair with a particular shape or configuration and function by applying a thin film of a resin or gum onto the hair to adhere adjacent hairs together so that they retain the particular shape or configuration at the time of application. Many of these hair sprays have been applied from aerosol compositions that include a liquifiable propellant gas—generally a halohydrocarbon, such as trichlorofluoromethane or trichlorotrifluoroethane or a gaseous hydrocarbon such as propane or butane. Recently-proposed legislation directed to the depletion of the atmospheric ozone layer has led to the halohydrocarbons being increasingly replaced with pure gaseous non-halogenated hydrocarbons as propellants. However, the use of non-halogenated hydrocarbons as propellants has resulted in a problem of decreased solubility of the hair spray resin or gum in water requiring an increased amount of a volatile organic solvent, such as ethanol, to achieve sufficient solubility, therefore creating an additional ecological problem.

As set forth in the Nuber et al. U.S. Pat. No. 4,767,613, film-forming polymers based on carboxyl-containing resins can be at least partially neutralized to improve the water solubility or dispersibility of the resin and provide the resin with the quality of being easier to remove from the hair during washing. However, as disclosed in the Nuber et al. U.S. Pat. No. 4,767,613, such aerosol hair treating agents generally have a maximum of about 5% water and require a high amount, up to about 95% by weight, of a volatile organic solvent, such as alcohol, despite the increased solubility of the neutralized resin.

Stepan Company of Northfield, Ill. discloses one example of an aerosol hair spray that includes 41.10% by weight water, but the aerosol composition also includes 45.70% by weight alcohol, as follows, where percentages are present by weight:

Terpolymer of polyvinyl pyrrolidone, ethylmethacylate, and methacrylic acid 9.60%; SDA 40 Alcohol (190 Proof) 45.70%; 2-methyl-2-amino-1-propanol (AMP) 0.40%; Silicone L-722 (Union Carbide) 0.50%; Propylene Glycol 2.00%; Perfume V-5177 (Van Dyke) 0.60%; 5% Morpholine in SDA 40 Alcohol 0.10%; and Distilled Water 41.10%.

In accordance with the present invention, a new and improved aqueous aerosol or non-aerosol hair styling aid composition has been found wherein fixative resins or gums can be suitably solubilized or dispersed in the aqueous composition containing about 30% to about 90% by weight water and less than 40% volatile organic compounds, particularly less than about 35% volatile organic compounds, e.g. 0-30% ethanol, preferably 5-25% alcohol, while providing an aerosol or non-aerosol styling aid or mousse that can effectively solubilize or disperse up to about 40% resin or gum, with a volatile organic solvent being optional for faster drying.

SUMMARY OF THE INVENTION

In brief, the present invention is directed to an aerosol or non-aerosol aqueous hair styling aid or mousse composition, and method, including a water-soluble or water-dispersable fixative resin in an amount of about 2% to about 40% by weight of the composition, particularly about 2% to about 15% by weight of the composition; an electrolyte; water in an amount of about 30% to about 90% by weight of the composition; alcohol in an amount of 0% to about 30% by weight; and, with the aerosol compositions, a liquified propellant gas, such as dimethyl ether, in an amount of about 5% to about 50% based on the total weight of the aerosol composition. When the fixative resin of the present invention includes one or more carboxylic acid moieties, the acid moieties should be neutralized about 30% to about 100% by weight.

Accordingly, one aspect of the present invention is to provide a new and improved hair treating composition, and method, that can be applied to the hair from an aqueous aerosol or non-aerosol composition in the form of a hair spray, mousse, foam or gel that provides hair setting compositions for retaining a particular shape or configuration of the hair.

Another aspect of the present invention is to provide an aerosol hair styling aid composition, and method, in the form of a hair spray, mousse, foam or gel that includes water in an amount of about 30% to about 90% by weight of the composition, a fixative resin that is solubilized or dispersed in an amount of about 2% to about 40% by weight of the composition, and a propellant gas.

Another aspect of the present invention is to provide an aerosol or non-aerosol hair styling aid composition, and method, in the form of a hair spray, mousse, foam or gel, that includes at least 30% by weight water, a fixative resin that includes a polymer that contains one or more vinyl or acrylate monomers, and a propellant for aerosol compositions.

Still another aspect of the present invention is to provide a new and improved aerosol or non-aerosol hair styling aid composition, that includes water in an amount of about 30% to about 90% by weight of the composition, a fixative resin that is solubilized or dispersed in an amount of about 2% to about 40% by weight of the composition, alcohol in an amount of 0-30%, preferably 5-25%, by weight, and a propellant gas for aerosol compositions.

A further aspect of the present invention is to provide a new and improved aerosol or non-aerosol hair styling aid composition, that includes water in an amount of about 30% to about 90% by weight of the composition, a fixative resin that is solubilized or dispersed in an amount of about 2% to about 40% by weight of the composition, alcohol in an amount of 0-30%, preferably 5-25%, by weight, a propellant gas, and a conditioning agent in an amount of about 0.1% to about 10% by weight of the composition.

BRIEF DESCRIPTION OF THE DRAWING

The drawing is a graph showing the viscosity of aqueous and hydroalcoholic solutions of a butyl ester of PVM/MA copolymer as a function of neutralization level and electrolyte concentration wherein the butyl ester of PVM/MA=4% by weight of the compositions, at a temperature of 30°±0.2° C.

DETAILED DESCRIPTION OF THE PREFERRED EMBODIMENT

Any of the following polymers that are soluble or dispersible in the aqueous phase may be used; if an optional co-solvent such as ethanol is present, the polymer should be soluble or dispersible in the combined solvent system. Solubility or dispersibility is determined at ambient conditions (e.g., a temperature of about 25° C. and atmospheric pressure).

The polymers or resins useful in the compositions of the present invention are homopolymers or copolymers that can be rendered dispersible or soluble in aqueous or hydroalcoholic solvent mixtures. To achieve the full advantage of the present invention, the fixative resin should be a synthetic, linear, homopolymer or random copolymer including at least one, and preferably two or more, vinyl or acrylate monomers of the following group:

Alkyl vinyl ethers
$R-O-CH=CH_2$     $R = $ alkyl $C_1-C_{10}$

Alkyl Acrylates
$$CH_2=CH-\overset{\overset{O}{\|}}{C}O-R \quad R\text{-alkyl } C_1-C_{10}$$

Vinyl esters
$$CH_2=CH-O\overset{\overset{O}{\|}}{C}-R \quad R=\text{alkyl } C_1-C_{10}$$

N-vinyl lactams
$$H_2C=C-N\underset{R.}{\overset{\overset{\displaystyle O}{\underset{\|}{C}}}{\diagup\!\!\!\diagdown}} \quad R=\text{alkylene } C_1-C_{10}$$

Alkyl acrylamides
$$H_2C=CH-\overset{\overset{O}{\|}}{C}-NH-R_1$$

$R_1$-alkylene $C_1-C_{10}$

Half vinyl esters/half amides
$$H_2C=CH-O-\overset{\overset{O}{\|}}{C}-R_1-\overset{\overset{O}{\|}}{C}-NH-R_2$$

$R_1 = $ alkylene $C_1-C_{10}$ $R = $ alkyl $C_1-C_{10}$

Half esters of maleic anhydride
$$\begin{array}{c} HC=CH-\overset{\overset{O}{\|}}{C}-O-R \\ | \\ O=C \\ | \\ OH \end{array}$$

$R = $ alkyl $C_1-C_{10}$

Acrylic acid
$$H_2C=CH-\overset{\overset{O}{\|}}{C}-OH$$

Crotonic acid
$$CH_3-CH=CH-\overset{\overset{O}{\|}}{C}-OH$$

Methacrylic acid
$$\begin{array}{c} CH_3 \\ | \\ CH_2=C \\ | \\ C=O \\ | \\ OH \end{array}$$

If the fixative resin is a copolymer, the copolymer preferably includes from about 5% to about 13% by weight of acrylic acid, crotonic acid, methacrylic acid or a combination thereof. In addition, in most copolymers, the ratio of water soluble monomers, such as N-vinyl lactams and acrylamides, in the polymer is maintained relatively low to reduce the tackiness and moisture sensitivity of the resin. For this reason and depending on the polymer, usually 5 to 15 acid units are required to render the polymer soluble in polar solvents, such as water, alcohols, ketones, glycol ethers, liquified dimethyl ether, and mixtures through neutralization with a suitable base.

Examples of preferred copolymers are the mono ethyl, isopropyl or n-butyl esters of poly(methyl vinyl ether/maleic acid); poly(vinyl pyrrolidone/ethyl methacrylate/methacrylic acid), poly(ethyl acrylate/acrylic acid/N-t-butyl acrylamide), and poly(vinyl acetate/crotonic acid). The compositions of the present invention preferably include from about 0.01% to about 15% resin to provide the best esthetics and spray delivery. Other suitable classes of polymers include anionic, nonionic, amphoteric and cationic polymers. Specific polymers include polyvinylpyrrolidone (PVP), copolymers of (PVP) and methylmethacrylate, copolymers of PVP and vinyl acetate (VA), polyvinyl alcohol (PVA), copolymers of PVA and crotonic acid, copolymers of PVA and maleic anhydride, hydroxypropyl cellulose, hydroxypropyl guar gum, sodium polystyrene sulfonate, PVP/ethylmethacrylate/methacrylic acid terpolymer and octylacrylamide/acrylate/butylaminoethyl methacrylate copolymers, and mixtures.

With certain of the acidic polymers, it may be necessary to neutralize some acidic groups to promote soubility/dispersibility, e.g., PVA/crotonic acid. Neutralization and increased solubilization are accomplished with one or more inorganic bases such as sodium hydroxide, potassium hydroxide, ammonium hydroxide and/or ammonium carbonate. Among stable organic bases are the water soluble bases such as monoethanolamine (MEA), diethanolamine (DEA), triethanolamine (TEA), 2-methyl-2-amino-1-propanol (AMP), monoamino glycols, and the like, which help solubilize the polymer in water solutions. The level of neutralization required for solubilization varies for each polymer. All of the above-described acidic polymers become soluble in water and hydroalcoholic solutions at 100% neutralization, and all described levels of water/alcohol/propellant solutions. The pH of these solutions usually ranges from 9 to 12. The lowest neutralization level needed to render the polymer water soluble or dispersible depends on the kind of polymer, and the amount of alcohol, water, and propellant. For instance, for poly(methyl vinyl ether/maleic acid) in water the lowest neutralization level is about 40% with sodium hydroxide and AMP; for poly(ethyl acrylate/acrylic acid/N-t-butyl acrylamide) the lowest neutralization level is about 75% with AMP and 65% with sodium hydroxide. At these neutralization levels, the pH of the solutions range from about 5 to about 7. A neutral pH such as this is preferred, however, the pH of the compositions of the present invention can vary from about 4 to about 13.

To achieve the full advantage of the present invention, an electrolyte should be soluble in the water or water and alcohol carriers and can be included in the composition for the purpose of lowering the viscosity of the composition to achieve a higher percentage of polymer in the composition; and to improve the aesthetics and ease of spraying from aerosol and pump sprays. Also, the electrolyte can stabilize the polymer in aqueous solution, by preventing the formation of aggregates, and thereby prolong formula stability. The electrolyte reduces the viscosity of the solution by eliminating intramolecular and intermolecular polymer interactions. In practice, lowering the viscosity of the compositions allows the easy and an aesthetic spraying of the formulation from aerosol containers and lowers the required force of actuation in pump sprayers. The electrolyte also serves to reduce or eliminate foaming during spraying of water and alcohol (hydroalcoholic) aerosol compositions.

The electrolyte salts useful in accordance with the present invention are inorganic salts, or organic salts and/or polyelectrolytes. The polyelectrolytes do not lower the viscosity of the composition to the same extent as the other electrolytes. These electrolytes include monovalent and divalent inorganic salts formed from alkali and alkaline earth metals of groups IA or IIA of the Periodic Table of the elements and halogens from group VII of the same table; or salts formed from alkali or alkaline earth metals of groups IA or IIA of the Periodic Table and mineral acids such as sulfuric, nitric, phosphoric, boric, carbonic, sulfurous, and/or phosphorous acids.

Preferred salts of metals from groups IA and IIA with mineral acids include: sodium sulfate, potassium sulfate, lithium sulfate, calcium sulfate, magnesium sulfate, sodium nitrate, potassium nitrate, lithium nitrate, calcium nitrate, magnesium nitrate, sodium bicarbonate and potassium bicarbonate. Ammonium chloride, ammonium bromide and ammonium bicarbonate also are useful as electrolytes.

Other preferred inorganic salts include sodium, potassium, ammonium, calcium, barium, zinc and magnesium chlorides, bromides, sulfates, and nitrates, particularly the chlorides and bromides.

Also useful are monovalent and divalent water-soluble organic salts of alkali and alkaline earth metals from groups IA and IIA of the Periodic Table and alkyl or aryl carboxylic, sulfuric, and/or sulfonic acids. Preferred salts are sodium and potassium methane and ethane sulfonates, sodium and potassium benzene and toluene sulfonates, sodium and potassium and calcium benzoates, and sodium and potassium acetates and propionates. Ammonium benzoate also is a useful salt.

Other preferred salts of metals from groups IA and IIA with organic aliphatic carboxylic acids include: lithium acetate, calcium acetate, magnesium acetate, sodium citrate (mono and tri salts), potassium citrate (mono and tri salts), lithium citrate (mono and tri salts) and ammonium citrate (mono and tri salts). Ammonium acetate also is useful.

Preferred salts of metals from groups IA and IIA with sulfonic acids include: sodium methanesulfonate, potassium methanesulfonate, sodium ethanesulfonate, potassium ethanesulfonate, ammonium ethanesulfonate, calcium methanesulfonate, sodium benzenesulfonate, potassium benzenesulfonate, sodium p-toluenesulfonate, potassium p-toluenesulfonate, and calcium p-toluenesulfonate. Ammonium methanesulfonate also is useful.

The level of electrolyte can vary in accordance with the desired physical properties of the composition. Levels from 0.001N to 1.0N are most useful. For most polymers, 0.001N to 0.01N levels of electrolyte are sufficient. The level of electrolyte salt depends on the polymer kind, pH and compatibility, desired degree of tackiness, alcohol level and hair hold desired.

In addition to the electrolyte salts, useful polyelectrolytes include the water-soluble polyester sodium sulfonates:

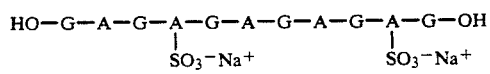

wherein
A = an aromatic dicarboxylic acid moiety and
G = an aliphatic or cycloaliphatic glycol residue;

sodium poly(styrene sulfonates):

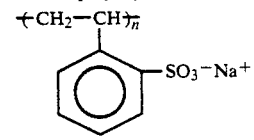

wherein n = 2 to about 2,400;

salts of polyacrylic acid, poly(methacrylic acid), and/or poly(maleic acid):

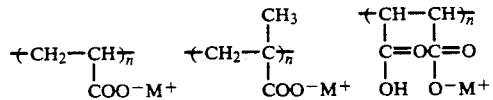

wherein
M = monovalent metal and
n = 2 to about 1,000.

Polysalts, such as salts of polyphosphoric acid, also can be used. These polysalts, due to their polymeric nature, also act as hair holding resins. Their level can be varied from about 0.001% to about 1% by weight. A polysalt level of about 0.001% to about 0.05% as the only electrolyte is sufficient in most cases to achieve optimal results.

Table I shows the viscosity of the following two compositions, with and without an electrolyte;

| | A (without electrolyte) Wt. % | B (with electrolyte) Wt. % |
|---|---|---|
| Water | 85.56 | 85.06 |
| Ethanol | 6.00 | 6.00 |
| Butyl ester of PVM/MA* | 6.00 | 6.00 |

| | A (without electrolyte) Wt. % | B (with electrolyte) Wt. % |
|---|---|---|
| AMP | 2.44 | 2.44 |
| NaCl | — | 0.50 |

*methyl vinyl ether/maleic anhydride copolymer.

TABLE I

Viscosities of 6% solutions of 100% neutralized butyl ester of PVM/MA copolymer in water. Viscosity was obtained using an Ubbelhode Capillary Viscometer, at 30° C. +/− 0.2° C. having a constant of K = 0.05 centistokes/second.

| No. | Family of Salt | Salt | Viscosity cs |
|---|---|---|---|
| 1. | No Salt | pure solution | 23.83 |
| 2. | Alkali Metal w/Halogen | with Sodium Chloride | 15.00 |
| 3. | Alkali Metal w/Halogen | with Sodium Bromide | 16.15 |
| 4. | Alkali Metal w/Halogen | with Ammonium Chloride | 13.79 |
| 5. | Alkali Metal w/Halogen | with Calcium Chloride | 11.54 |
| 6. | Metals w/Mineral Acid | with Sodium Sulfate | 15.44 |
| 7. | Metals w/Organic Aliphatic Carboxylic Acids | with Ammonium Acetate | 15.14 |
| 8. | Metals w/Organic Aromatic Carboxylic Acids | with Sodium Benzoate | 16.14 |
| 9. | Metals w/Sulfonic Acids | with Xylene Ammonium Sulfonate | 16.83 |
| 10. | Polyelectrolytes | with Sodium Polyestyrene Sulfonate (M.W. 70,000) | 23.20 |

The fixative polymer(s) is used at a level of from about 0.25% to about 40% by weight, generally about 2% to about 15% by weight, and preferably from about 1% to about 8% by weight of the total composition. The weight average molecular weight of the polymer is not critical but is generally in the range of from about 2,000 to about 2,000,000.

In accordance with one important embodiment of the present invention, the composition of the present invention also includes from about 0.1% to about 10%, particularly about 0.5% to about 10%, and preferably from about 1.0% to about 5.0%, by weight of a non-volatile silicone compound or other conditioning agent(s), preferably a water-insoluble, emulsifiable conditioning agent. The preferred non-volatile silicone compound is a polydimethylsiloxane compound, such as a mixture, in about a 3:1 weight ratio, of a low molecular weight polydimethylsiloxane fluid and a higher molecular weight polydimethylsiloxane gum. The non-volatile polydimethylsiloxane compound is added to the composition of the present invention in an amount sufficient to provide improved combing and improved feel (softness) to the hair after shampooing. As referred to herein, "silicone gums" are those nonfunctional siloxanes having a viscosity of from about 5 to about 600,000 centistokes at 25° C. The so-called rigid silicones, as described in U.S. Pat. No. 4,902,499, herein incorporated by reference, having a viscosity above 600,000 centistokes at 20° C., e.g. 700,000 centistokes plus, and a weight average molecular weight of at least about 500,000 also are useful in accordance with the present invention.

Preferred silicone gums include linear and branched polydimethylsiloxanes, of the following general formula:

$$(CH_3)_3SiO-[Si(CH_3)_2O]_n-Si(CH_3)_3,$$

wherein n is from about 2,000 to about 15,000, preferably from about 2,000 to about 7,000. Silicone gums useful in compositions of the present invention are available from a variety of commercial sources, including General Electric Company and Dow Corning.

Another particularly suitable conditioning agent that can be included in the composition of the present invention is a volatile hydrocarbon, such as a hydrocarbon including from about 10 to about 30 carbon atoms, that has sufficient volatility to slowly volatilize from the hair after application of the aerosol or non-aerosol styling aid composition. The volatile hydrocarbons provide essentially the same benefits as the silicone conditioning agents.

The preferred volatile hydrocarbon compound is an aliphatic hydrocarbon including from about 12 to about 24 carbon atoms, and having a boiling point in the range of from about 100° C. to about 300° C. Exemplary volatile hydrocarbons are depicted in general structural formula (I), wherein n ranges from 2 to 5,

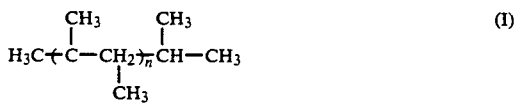

Examples of volatile hydrocarbons useful in the composition of the present invention are the commercially-available compounds PERMETHYL 99A and PERMETHYL 101A, corresponding to compounds of general structure (I) wherein n is 2 and 3, respectively, available from Permethyl Corporation, Frazer, Pa. A volatile hydrocarbon compound is useful in the composition of the present invention either alone, in combination with another volatile hydrocarbon, or in combination with a volatile silicone.

Examples of other suitable water-insoluble conditioning agents that can be incorporated into the aerosol or non-aerosol aqueous styling aid composition of the present invention include the following: polysiloxane polyether copolymers; polysiloxane polydimethyl dimethylammonium acetate copolymers; acetylated lanolin alcohols; dimethyl dialkyl ammonium chlorides; modified alkyl dimethyl benzyl ammonium chlorides; lauryl dimethylamine oxide; stearyl dimethyl benzyl ammonium chloride; a lanolin-derived extract of sterol on sterol esters; lanolin alcohol concentrate; an isopropyl ester of lanolin fatty acids; sulfur rich amino acid concentrates; isopropyl ester of lanolin fatty acids; stearyl dimethyl benzyl ammonium chloride; cetyl trimethyl ammonium chloride; oleyl dimethyl benzyl ammonium chloride; oleyl alcohol; stearyl alcohol; stearyl dimethyl benzyl ammonium chloride; stearamidopropyl dimethyl myristyl acetate; a polyol fatty acid; a fatty amido amine; guar hydroxypropyltrimonium chloride; cetyl/stearyl alcohol; quaternized protein; keratin protein derivatives; isostearamidopropyl dimethylamine; stearamidopropyl dimethylamine; cetrimonium bromide; myrtrimonium bromide; stearalkonium chloride; cetyl trimethyl ammonium chloride; laurylpyridinium chloride; tris(oligoxyethyl)alkyl ammonium phosphate; an aminofunctional silicone; lapyrium chloride; isopropyl ester of lanolic acids; ethoxylated (30) castor oil; acetylated lanolin alcohol; fatty alcohol fraction of lanolin; a mineral oil and lanolin alcohol mixture; high molecular weight esters of lanolin; quaternium-75; vinylpyrrolidone/dimethylaminoethylmethacrylate copolymer; alkyl trimethyl ammonium chloride; 5 mole ethylene oxide adduct of soya sterol; 10 mole ethylene oxide adduct of soya sterol; stearic acid ester of ethoxylated (20 mole) methyl glucoside; sodium salt of polyhydroxycarboxylic acid; hydroxylated lanolin; cocamidopropyl dimethylamine lactate; cocamidopropyl dimethylamine propionate; cocamidopropyl morpholine lactate; isostearamidopropyl dimethylamine lactate; isostearamidopropyl morpholine lactate; oleamidopropyl dimethylamine lactate; linoleamidopropyl dimethylamine lactate; stearamidopropyl dimethylamine lactate, ethylene glycol monostearate and propylene glycol mixture; stearamidopropyl dimethylamine lactate; acetamide MEA; lactamide MEA; stearamide MEA; behenalkonium chloride; behenyl trimethyl ammonium methosulfate and cetearyl alcohol mixture; cetearyl alcohol; isostearamidopropalkonium chloride; linoleamidopropalkonium chloride; oleyl dimethyl benzyl ammonium chloride; tallow imidazolinum methosulfate; stearyl dimethyl benzyl ammonium chloride; stearyl trimonium methosulfate; mixed ethoxylated and propoxylated long chain alcohols; stearamidopropyl dimethylamine lactate; polonitomine oxide; oleamine oxide; stearamine oxide; soya ethyldimonium ethosulfate; hydroxypropyl bislauryl-dimonium chloride; hydroxypropyl biscetyl-dimonium chloride; hydroxypropyl bisstearyl dimonium chloride; hydroxypropyl bisbehenyl dimonium chloride; ricinolamidopropyl ethyldimonium ethosulfate; olealkonium chloride; stearalkonium chloride; N-(3-isostearamidopropyl)-N,N-dimethyl amino glycolate; N-(3-isostearamidopropyl)-N,N dimethyl amino gluconate; hydrolyzed animal keratin; ethyl hydrolyzed animal keratin; stearyl ammonium chloride; stearamidoethyl diethylamine; cocamidopropyl dimethylamine; lauramidopropyl dimethylamine; oleamidopropyl dimethylamine; palmitamidopropyl dimethylamine; stearamidopropyl dimethylamine lactate; avocado oil; sweet almond oil; grape seed oil; jojoba oil; apricot kernel oil; sesame oil; hybrid safflower oil; wheat germ oil; cocamidoamine lactate; ricinoleamido amine lactate; stearamido amine lactate; stearamido morpholine lactate; isostearamido amine lactate; isostearamido morpholine lactate; wheat germamido dimethylamine lactate; behenamidopropyl betaine; ricinoleamidopropyl betaine; wheat germamidopropyl dimethylamine oxide; disodium isostearaimido MEA sulfosuccinate; disodium oleamide PEG-2 sulfosuccinate; disodium oleamide MEA sulfosuccinate; disodium ricinoleyl MEA sulfosuccinate; disodium wheat germamido MEA sulfosuccinate; disodium wheat germamido PEG-2 sulfosuccinate; stearalkonium chloride; stearly dimethyl benzyl ammonium chloride; stearamido amine; stearamido morpholine; isostearamido amine; isostearamido morpholine; polyethylene glycol (400) mono and distearates; synthetic calcium silicate; isostearic alkanolamide; ethyl esters of hydrolyzed animal protein; blend of cetyl and stearyl alcohols with ethoxylated cetyl or stearyl alcohols; amido amines; polyamido amines; palmityl amido betaine; propoxylated (1–20 moles) lanolin alcohols; isostearamide DEA; and hydrolyzed collagen protein.

When one or more of these water-insoluble conditioning agents is included in the composition of the present invention in an amount of about 0.5% to about 10% by total weight of the composition, the composition also can include a suspending agent for the conditioning agent, in an amount of about 0.5% to about 10%, by total weight of the composition. The particular suspending agent is not critical and can be selected from any materials known to suspend water-insoluble liquids in shampoo compositions. Suitable suspending agents are for example, distearyl amate (distearyl phthalamic acid); fatty acid alkanolamides; esters of polyols and sugars; polyethylene glycols; the ethoxylated or propoxylated alkylphenols; ethoxylated or propoxylated fatty alcohols; and the condensation products of ethylene oxide with long chain amides. These suspending agents, as well as numerous others not cited herein, are well known in the art and are fully described in the literature, such as McCUTCHEON'S DETERGENTS AND EMULSIFIERS, 1989 Annual, published by McCutcheon Division, MC Publishing Co.

A nonionic alkanolamide also is optionally included in an amount of about 0.1% to about 5% by weight in the aerosol styling aid compositions that include a conditioning agent to provide exceptionally stable emulsification of water-insoluble conditioning agents and to aid in thickening and foam stability. Other useful suspending and thickening agents can be used instead of the alkanolamides such as sodium alginate; guar gum; xanthan gum; gum arabic; cellulose derivatives, such as methylcellulose, hydroxybutylcellulose, hydroxyethylcellulose, hydroxypropylcellulose and carboxymethylcellulose; and various synthetic polymeric thickeners, such as the polyacrylic acid derivatives. Suitable alkanolamides include, but are not limited to, those known in the art of hair care formulations, such as cocamide monoethanolamide (MEA), cocamide diethanolamide (DEA), soyamide DEA, lauramide DEA, oleamide monoisopropylamide (MIPA), stearamide MEA, myristamide MEA, lauramide MEA, capramide DEA, ricinoleamide DEA, myristamide DEA, stearamide DEA, oleylamide DEA, tallowamide DEA, lauramide MIPA, tallowamide MEA, isostearamide DEA, isostearamide MEA and combinations thereof. Other suitable suspending agents are disclosed in Oh et al. U.S. Pat. No. 4,704,272; Grote et al. U.S. Pat. No. 4,741,855; and Bolich, Jr. et al. U.S. Pat. No. 4,788,006, which patents are hereby incorporated by reference.

Emulsion stabilizers also may be used in compositions of the invention. Useful examples include, such compounds as polyethylene glycol, silicone copolyols, polyvinyl alcohol, sorbitan monostearate, oleth-2, sorbitan monolaurate, and nonionic block copolymers of ethylene oxide and propylene oxide such as those marketed by BASF Wyandotte under the name PLURONICS ®. When present, such stabilizers comprise from about 0.05% to about 1%, preferably from about 0.1% to about 0.8%, by weight of the composition.

The propellant gas included in the aerosol compositions of the present invention can be any liquefiable gas conventionally used for aerosol containers. Examples of materials that are suitable for use as propellants are trichlorofluoromethane, dichlorodifluoromethane, dichlorotetrafluoroethane, monochlorodifluoromethane, trichlorotrifluoroethane, dimethyl ether, propane, n-butane and isobutane, used singly or admixed. Water-soluble gases such as dimethyl ether, carbon dioxide, and/or nitrous oxide also can be used to obtain aerosols having reduced flammability.

Water-immiscible, liquified, hydrocarbon and halogenated hydrocarbon gases such as propane, butane and chlorofluorocarbons can be used advantageously to deliver the contents of the aerosol container without the dramatic pressure drops associated with other immiscible gases. Here there is no concern for the head space to be left inside the aerosol container, because the liquified gas will sit on top of the aqueous formulation and the pressure inside the container is always the vapor pressure of saturated hydrocarbon vapor.

Other insoluble, compressed gases such as nitrogen, helium and fully-flourinated oxetanes and oxepanes also are useful to deliver the compositions from aerosol containers. Other means of delivery of the above-described aqueous styling aid compositions include, pump sprayers, all forms of bag-in-can devices, in situ carbon dioxide ($CO_2$) generator systems, compressors, and the like.

The amount of the propellant gas is governed by normal factors well known in the aerosol art. For mousses, the level of propellant is generally from about 3% to about 30%, preferably from about 5% to about 15% of the total composition. If a propellant such as dimethyl ether utilizes a vapor pressure suppressant (e.g., trichlorethane or dichloromethane), for weight percentage calculations, the amount of suppressant is included as part of the propellant.

The aerosol compositions also can contain a variety of other nonessential, optional components suitable for rendering such compositions more acceptable. Such conventional optional ingredients are well known to those skilled in the art, e.g., other emulsifiers such as anionics (e.g., sodium alkyl sulfate); preservatives such as benzyl alcohol, methyl paraben, propyl paraben and imidazolidinylurea; cationic emulsifiers/conditioners such as cetyl trimethyl ammonium chloride, stearyldimethyl benzyl ammonium chloride, and di(partially-hydrogenated tallow) dimethylammonium chloride; thickeners and viscosity modifiers such as a diethanolamide of a long chain fatty acid, fatty alcohols (i.e., cetearyl alcohol), sodium chloride, sodium sulfate, and ethyl alcohol; pH adjusting agents such as citric acid, succinic acid, sodium hydroxide and triethanolamine; coloring agents such as any of the FD&C or D&C dyes; hair oxidizing (bleaching) agents such as hydrogen peroxide, perborate salts and persulfate salts; hair reducing agents such as thioglycolates; perfume oils; chelating agents such as ethylenediaminetetraacetic acid; and, among many other agents, polymer plasticizing agents such as glycerin and propylene glycol. These optional materials are generally used individually at a level of from about 0.01% to about 19%, preferably from about 0.5% to about 5% by weight of the total composition.

The aqueous formulations of the present invention also can contain the conventional hair spray adjuvants in amounts which generally range from about 0.1 to 2% by weight and preferably about 0.75 to 1% by weight. Among the additives which can be used are plasticizers such as glycols, phthalate esters and glycerine; silicones; emollients; lubricants and penetrants such as various lanolin compounds; protein hydrolysates and other protein derivatives; ethylene adducts and polyoxyethylene cholesterol; dyes, tints and other colorants; and perfumes.

The optional alcohol employed in the composition is an aliphatic straight or branched chain monohydric alcohol having 2 to 4 carbon atoms. Isopropanol and especially ethanol are preferred. The concentration of the alcohol in the composition should be less than about 40% by weight, and surprisingly can be as low as 0%, preferably 0—30% by weight and more preferably 5-20% by weight. Some alcohol, in an amount of about 2% to about 10% by weight provides faster drying of the styling aid after application to the hair.

What is claimed is:

1. A non-foaming aqueous aerosol hair spray composition consisting essentially of a fixative resin that is a linear homopolymer or random copolymer including a monomer selected from the group consisting of a vinyl monomer and an acrylate monomer in an amount of about 2% to about 40% by weight of the composition; a water-soluble electrolyte selected from the group consisting of inorganic salts of alkali metals, inorganic salts of alkaline earth metals, organic salts of alkali metals, organic salts of alkaline earth metals, mineral acid salts, ammonium salts, polyelectrolytes, and mixtures in an amount of at least about 0.001N; water in an amount of about 30% to about 90% by weight of the composition; 0–30% alcohol; and a propellant selected from the group consisting of trichlorofluoromethane, dichlorodifluoromethane, dichlorotetrafluoroethane, monochlorodifluoromethane, trichlorotrifluoroethane, dimethyl ether, propane, n-butane, isobutane, carbon dioxide, nitrous oxide, nitrogen, helium, fluorinated oxetane, fluorinated oxepane, and mixtures thereof, in an amount of about 30% to about 50% by weight of the composition.

2. The composition of claim 1 further including a conditioning agent in an amount of about 0.1% to about 10% by weight of the composition.

3. The composition of claim 1, wherein the conditioning agent is water-insoluble and is selected from the group consisting of a silicone conditioning agent, a volatile hydrocarbon conditioning agent, and mixtures thereof.

4. The composition of claim 1 further including a water-insoluble alkanolamide in an amount of about 0.1% to about 5% by weight of the composition.

5. The composition of claim 1 further including an emulsion stabilizer in an amount of about 0.05% to about 3% by weight of the composition selected from the group consisting of a glycol, glycerine, a silicone copolyol, polyvinyl alcohol, sorbitan monostearate, oleth-2, sorbitan monolaurate, a copolymer of ethylene oxide and propylene oxide, and mixtures thereof.

6. The composition of claim 1, wherein the alcohol is a straight or branched chain monohydric alcohol having 2 to 4 carbon atoms and is included in the composition in an amount of about 1% to about 30% by weight of the composition.

7. The composition of claim 1, wherein the alcohol is included in an amount of about 5% to about 35% by weight of the composition.

8. The composition of claim 1, wherein the electrolyte is included in an amount of about 0.001N to about 1.0N.

9. The composition of claim 1, wherein the electrolyte is selected from the group consisting of ammonium, calcium, barium, and magnesium chloride, bromide, sulfate or nitrate.

10. The composition of claim 1, wherein the electrolyte is selected from the group consisting of sodium methanesulfonate, potassium methanesulfonate, sodium ethanesulfonate, potassium ethanesulfonate, sodium benzenesulfonate, potassium benzenesulfonate, sodium toluenesulfonate, potassium ethanesulfonate, ammonium methanesulfonate, sodium benzoate, potassium benzoate, sodium acetate, potassium acetate, sodium propionate, potassium propionate, and mixtures thereof.

11. The composition of claim 1, wherein the electrolyte is a polyelectrolyte selected from the group consisting of a polyester sodium sulfonate; a sodium poly(styrene sulfonate); a poly(acrylic acid) salt; a poly(methacrylic acid) salt; a poly(maleic acid) salt; and mixtures thereof.

12. The composition of claim 1, wherein the monomer is selected from the group consisting of alkyl vinyl ethers, alkyl acrylates, vinyl alkyl esters, N-vinyl lactams, alkyl acrylamides, half vinyl esters/half amides, half esters of maleic anhydride, acrylic acid, crotonic acid, methacrylic acid, and mixtures thereof.

13. The composition of claim 1, wherein the fixative resin is a copolymer containing at least two monomers selected from the group consisting of alkyl vinyl.

* * * * *

UNITED STATES PATENT AND TRADEMARK OFFICE
CERTIFICATE OF CORRECTION

PATENT NO. : 5,164,177
DATED : Nov. 17, 1992
INVENTOR(S) : Darshna Bhatt, et al

It is certified that error appears in the above-indentified patent and that said Letters Patent is hereby corrected as shown below:

Column 3, line 46, in the last line of the formula --  -- should be inserted between "N" and "R" and should read as follows -- N R --;

Column 3, line 61, delete "R =" and substitute therefor -- $R_2 =$ --;

Column 8, line 5, in the formula, delete "(CH$_3$)2O" and substitute therefor -- (CH$_3$)$_2$O --;

Column 12, line 33, after "claim" delete "1," and substitute therefor -- 2, --.

Signed and Sealed this

Twenty-sixth Day of July, 1994

Attest:

BRUCE LEHMAN

Attesting Officer

Commissioner of Patents and Trademarks